(12) United States Patent
Powell

(10) Patent No.: US 8,073,612 B2
(45) Date of Patent: *Dec. 6, 2011

(54) ROTATIONAL GENERATION TYPE WIRELESS OXYGEN SENSOR

(75) Inventor: Patrick Powell, Farmington Hills, MI (US)

(73) Assignee: DENSO International America, Inc., Southfield, MI (US)

( * ) Notice: Subject to any disclaimer, the term of this patent is extended or adjusted under 35 U.S.C. 154(b) by 386 days.

This patent is subject to a terminal disclaimer.

(21) Appl. No.: 12/366,896

(22) Filed: Feb. 6, 2009

(65) Prior Publication Data

US 2010/0199637 A1   Aug. 12, 2010

(51) Int. Cl.
*F02D 45/00* (2006.01)
*F01N 11/00* (2006.01)

(52) U.S. Cl. .................... 701/109; 701/102; 60/277

(58) Field of Classification Search ............ 701/109, 701/115, 1, 2, 31, 32, 51; 123/672; 60/274–278, 60/284, 285; 73/114.72, 114.73; 204/406, 204/424, 426, 431; 455/419, 420
See application file for complete search history.

(56) References Cited

U.S. PATENT DOCUMENTS

| | | |
|---|---|---|
| 6,642,720 B2 | 11/2003 | Maylotte et al. |
| 6,662,642 B2 | 12/2003 | Breed et al. |
| 6,663,011 B1 | 12/2003 | Entleutner |
| 6,928,348 B1 * | 8/2005 | Lightner et al. ............... 701/33 |
| 6,988,026 B2 | 1/2006 | Breed et al. |
| 7,039,491 B1 | 5/2006 | Delbrugge, Jr. |
| 7,127,935 B2 | 10/2006 | Bonne et al. |
| 7,231,180 B2 | 6/2007 | Benson et al. |
| 7,286,058 B1 | 10/2007 | Gologorsky |
| 7,313,467 B2 | 12/2007 | Breed et al. |
| 7,579,589 B2 * | 8/2009 | Miller et al. ................. 250/292 |
| 2005/0145013 A1 * | 7/2005 | Hayashi et al. .............. 73/31.05 |
| 2006/0150713 A1 * | 7/2006 | Brown .......................... 73/23.31 |
| 2006/0171865 A1 * | 8/2006 | Quackenbush ............... 422/168 |
| 2007/0277605 A1 * | 12/2007 | Fouts et al. .................... 73/431 |
| 2009/0227887 A1 * | 9/2009 | Howard et al. ............... 600/531 |
| 2010/0222939 A1 * | 9/2010 | Namburu et al. ................. 701/2 |

* cited by examiner

*Primary Examiner* — John T. Kwon
*Assistant Examiner* — Johnny Hoang
(74) *Attorney, Agent, or Firm* — Harness, Dickey & Pierce, PLC

(57) ABSTRACT

An oxygen sensor for a motor vehicle having an electrode within an outer shell measures oxygen in exhaust gas exiting the vehicle and generates a signal based on the oxygen measurement. A communication device, powered by a battery or capacitor, wirelessly transmits the measured amount of oxygen from the electrode to a powertrain control module. The flow of exhaust gas through the exhaust system spins blades to spin a generator in a rotational power generation device to generate electrical current to be stored and used by the battery or capacitor. The rotational power generation device may be located in the exhaust pipe, such as through an exhaust pipe wall, and either be connected to the oxygen sensor shell or separate and connected only with electrical wires between the generator and the battery or capacitor.

20 Claims, 5 Drawing Sheets

ROTATIONAL GENERATION TYPE WIRELESS OXYGEN SENSOR

FIELD

The present disclosure relates to a self-powered oxygen sensor and, more particularly to a wireless oxygen sensor using a rotational device to generate electrical power for the sensor.

BACKGROUND

This section provides background information related to the present disclosure which is not necessarily prior art. Oxygen sensors may be used in automotive vehicle applications to improve fuel economy, ensure smooth performance, and reduce exhaust emissions. Oxygen sensors are typically located in the exhaust system before and after the exhaust catalyst in order to determine catalyst efficiency. In this way, pre-catalyst and post-catalyst signals may be monitored and adjusted to meet emissions regulations. Most vehicles today include from two to four oxygen sensors, but additional sensors may be used as tail pipe gas emission regulations become more stringent to improve the quality of tail pipe gas emissions.

In operation, oxygen sensors may have a ceramic cylinder tip to measure the proportion of oxygen in the exhaust gas flowing out of the engine. Oxygen sensor measurements are most accurate when the sensor is heated to a specific temperature range, or a specific temperature, such as approximately 800° C. (1,472° F.). Accordingly, each sensor may include at least one heating element to allow the sensor to reach an ideal temperature more quickly, such as when the exhaust is cold, such as at initial engine start-up. The temperature of the ceramic portion of the sensor may vary with respect to the exhaust gas temperature in order to maintain accuracy of the sensor signal.

After measuring the proportion of oxygen in the exhaust gas, the sensor then generates a voltage signal representing the difference between the exhaust gas and the air external to the internal combustion engine (i.e. air-fuel ratio). Depending on the style of sensor, the sensor may instead create a change in resistance signal to convey the same information. The signal is transmitted through signal wires to a powertrain control module (PCM) where the signal is compared with the stoichiometric air-fuel ratio (e.g. 14.7:1 by mass for gasoline) to determine if the air-fuel ratio is rich (e.g. unburned fuel vapor) or lean (e.g. excess oxygen). The PCM can then vary the fuel injector output to affect the desired air-fuel ratio and to ultimately optimize engine performance.

The sensor is typically powered through the various attached wires. For example, signal wires and heater wires may be used to provide power to the sensor and the heating elements, respectively. As exhaust gas emissions regulations become more stringent and more sensors, as a result, are used, additional wiring may be necessary. Additional wiring may provide added complexity, increased assembly costs, and increased natural resource consumption (e.g. copper and plastics). Additionally, sensor failure may occur at the various sensor wires (e.g. power wires, heater wires) due to improper wiring, connector corrosion, or wire failure. When the oxygen sensor fails, the PCM can no longer sense the air-fuel ratio. Vehicle performance may be impacted and excess fuel, such as gasoline, may be consumed by the engine.

SUMMARY

This section provides a general summary of the disclosure, and is not a comprehensive disclosure of the full scope and features of the disclosure. An oxygen sensor device may have an electrode within an outer shell for measuring oxygen in an exhaust gas exiting the vehicle. A signal may be generated by the oxygen sensor that is based on the oxygen measurement. A communication device, powered by an energy storage device, such as a capacitor or battery, or powered directly from a power generation device, may wirelessly transmit the measured amount of oxygen from the electrode to a powertrain control module. An amount of the exhaust gas may spin or rotate a generator in a rotational power generation device to generate an electrical current that may be stored in an energy storage device, such as a capacitor or battery.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. These example embodiments will now be described more fully with reference to the accompanying drawings.

Figure 1:
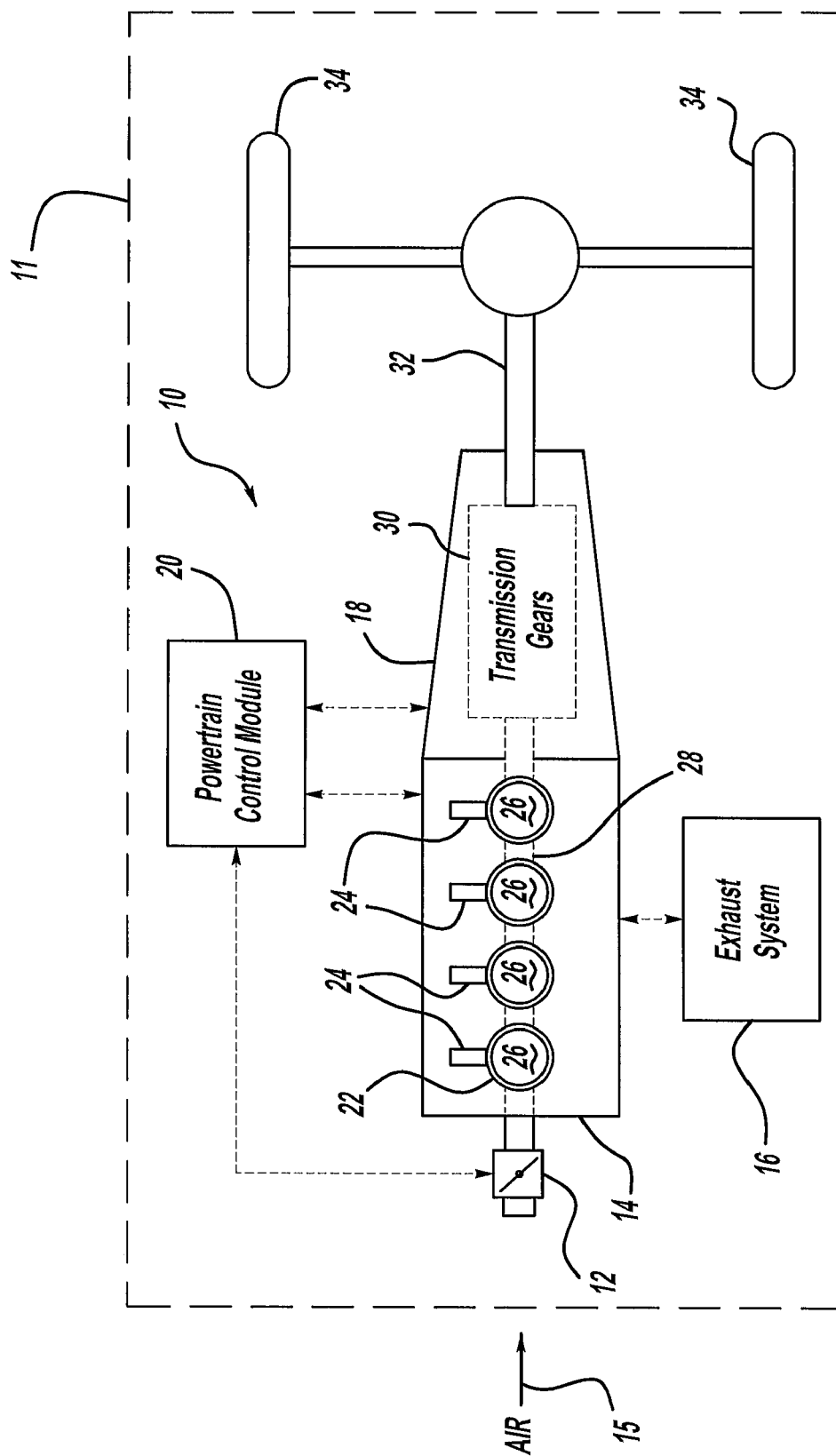
FIG. 1 is a functional block diagram of a vehicle drive system according to the present disclosure.

FIG. 1 depicts an exemplary vehicle drive system 10 of a vehicle 11. The vehicle drive system 10 includes a throttle valve 12, an engine 14, an exhaust system 16, an automatic transmission 18, and a powertrain control module (PCM) 20. Air enters the vehicle drive system 10 through the throttle valve 12, which under direction from the PCM 20, regulates the amount of air flowing into the engine 14. The intake air 15 is evenly distributed to N cylinders or combustion chambers 22 located in the engine 14. Although FIG. 1 depicts the engine 14 having four combustion chambers 22 (N=4), it should be understood that the engine 14 may include additional or fewer chambers 22. For example, the engine 14 may include from 1 to 16 chambers 22. Additionally, although PCM 20 is depicted, the functions of the PCM 20 could also be split between an engine control module (ECM) and a transmission control module (TCM).

Continuing with reference to FIG. 1, the air 15 entering the engine 14 combusts with fuel, which is provided by fuel injectors 24, in the combustion chambers 22. The PCM 20 varies the output of the fuel injectors 24 to optimize engine 14 performance. The combustion of the fuel and air reciprocally drives pistons 26 located within the combustion chambers 22. The reciprocating pistons 26 rotatably drive a crankshaft 28, which in turn, drives the transmission 18. The transmission 18 translates the drive torque through a series of gears 30 utilizing a plurality of gear ratios (e.g. 3-speed, 4-speed, 5-speed, 6-speed, etc.) to an output driveshaft 32. The driveshaft 32 then distributes the drive torque to vehicle wheels 34.

The combustion of fuel and air creates waste exhaust gases that are generally relatively harmless. However, a small amount of the gases include noxious or toxic pollutants, such as carbon monoxide (CO), hydrocarbons (HC), and nitrogen oxides ($NO_x$), that must be conveyed away from the engine 14 through the exhaust system 16.

Figure 2:
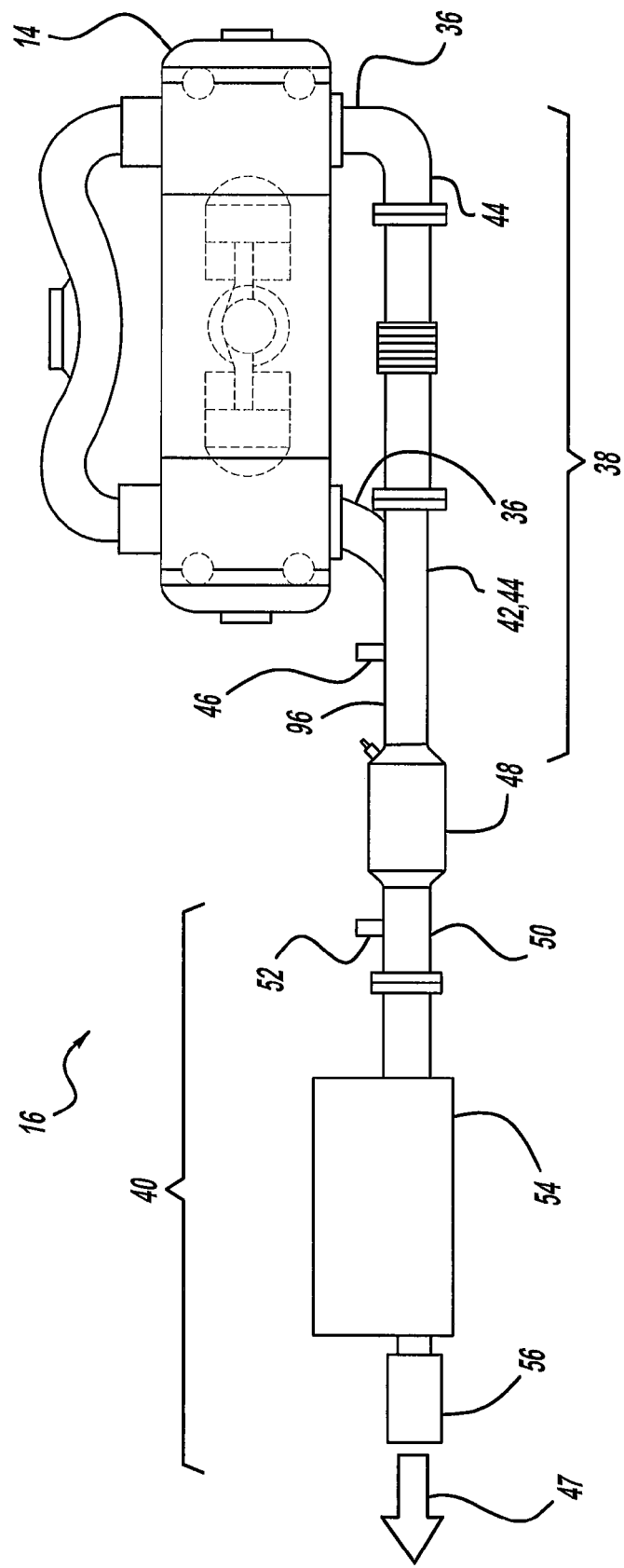
FIG. 2 is a perspective view of a vehicle exhaust system according to the present disclosure.

Referring now to FIG. 2, the exhaust system 16 includes an exhaust manifold 36, a mid-pipe region 38, and a cat-back region 40. The exhaust manifold 36 acts as a funnel to collect the exhaust gases from the combustion chambers 22 and release them through a single opening 42 into a downpipe 44 in the mid-pipe region 38. Once in the downpipe 44, the exhaust gases pass a first oxygen sensor 46 and a front exhaust pipe 96 before entering a catalytic converter 48. The catalytic converter 48 provides an environment for a chemical reaction whereby the exhaust gases are converted to less toxic substances. The reacted exhaust gases are then sent to a rear exhaust pipe 50 in the cat-back region 40 where they pass a second oxygen sensor 52. Once in the rear exhaust pipe 50, the reacted exhaust gases are sent to a muffler 54 for reducing noise from engine-generated sound waves that travel in the exhaust gases. This noise reduction assures that the noise emissions comply with acceptable levels. After exiting the muffler 54, the exhaust gases are expelled to the environment through an outlet 56. The outlet 56 emits the exhaust gases past the end of the vehicle 11, preventing exhaust gas from entering the vehicle cabin.

While the exhaust system 16 of the present embodiment is depicted as having a single exit path, it should be understood that the arrangement of the exhaust system 16 may vary. Vehicle space availability and engine type/size will dictate various other exhaust system modifications including, but not limited to, alternate pipe configurations, added components (e.g. an additional catalytic converter, a resonator, a turbocharger, etc), and/or a duplicated system. For example, in a six-cylinder "vee" (e.g. V-6) engine arrangement it is common to mirror the exhaust system 16 on both sides of the vehicle. In this way, three cylinders utilize one exhaust system, while the remaining three cylinders utilize an alternate exhaust system. The mirrored exhaust systems may be connected together through piping to utilize common components (e.g. a single tail pipe).

Figure 3:
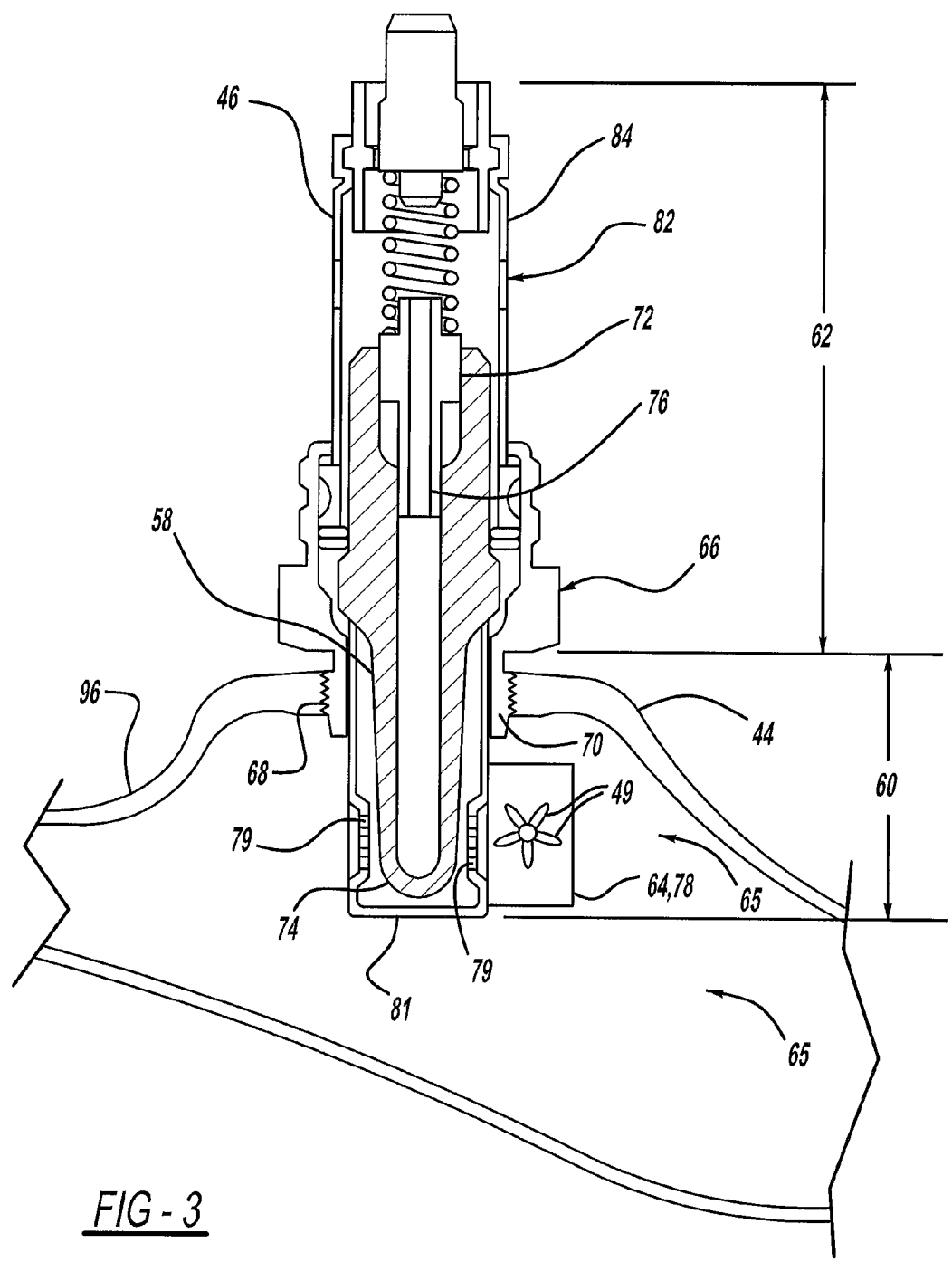
FIG. 3 is a cross-sectional view of an oxygen sensor in the exhaust system according to the present disclosure.
Figure 4:
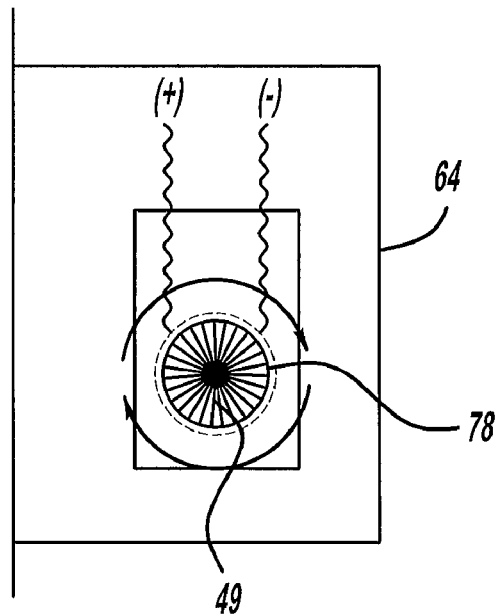
FIG. 4 is a schematic view of a rotational power generation device according to the present disclosure.
Figure 5:
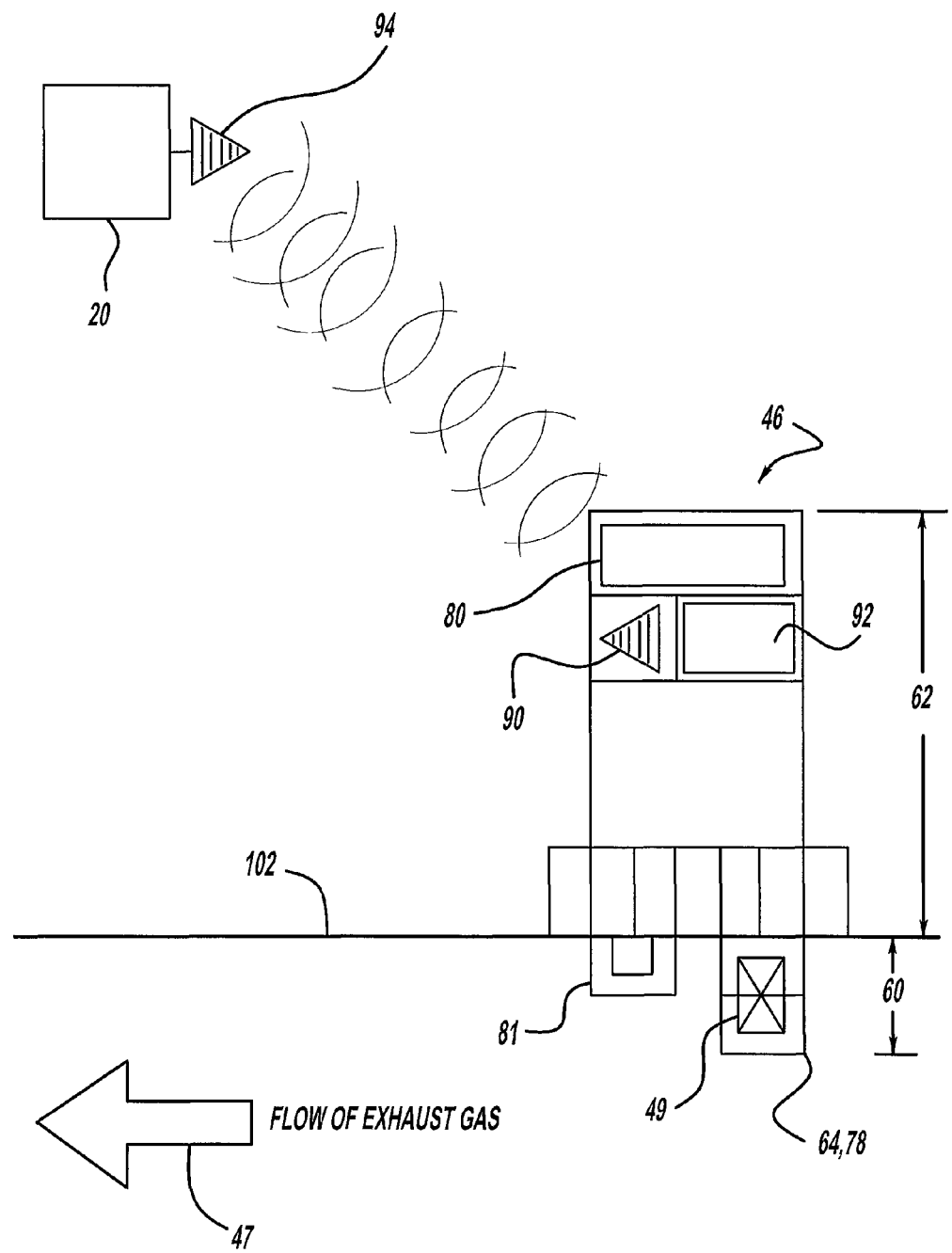
FIG. 5 is an enlarged view of part of the oxygen sensor of FIG. 3 and communication with a powertrain control module.

Referring now to FIGS. 3-5, the exhaust system 16 at the interface between the downpipe 44 and the first oxygen sensor 46 is depicted in greater detail. It will be appreciated that the first oxygen sensor 46 may function and/or be constructed in a similar manner to the second oxygen sensor 52.

The oxygen sensor 46 may include an electrode 58, a tip region 60, a cap region 62, and a rotational power generation device 64. A tool (not depicted) receives a nut 66, located in the cap region 62, to screw the oxygen sensor 46 into a threaded hole 68 located in the downpipe 44. A threaded collar 70 in the tip region 60 locates and removably attaches the oxygen sensor 46 to the threaded hole 68. Once seated, the electrode 58 and the rotational power generation device 64 protrude a predetermined distance into the downpipe 44 and into the flow path of exhaust gas 65 exiting the exhaust system 16. The electrode 58 may be a zirconium dioxide ($ZrO_2$, zirconia) ceramic material plated on inner and outer surfaces 72, 74 with porous platinum. When the electrode 58 is cold, the zirconia ceramic material behaves similar to an insulator. However, at elevated temperatures the zirconia ceramic material behaves as a semi-conductor and generates a voltage output. A heating element 76, encased in the electrode 58, raises the temperature of the electrode 58 to a conductive level in order to alleviate this problem during cold exhaust temperature periods (e.g. at engine startup). At the conductive temperature for the zirconia ceramic (~310° C.), the electrode 58 develops an electrical charge as oxygen ions pass through it.

In operation, the exhaust gases 65 exiting the exhaust system 16 may first pass through the rotational power generation device 64 and rotatably drive a generator 78. Rotation of the generator 78 creates electric current, which is used to charge an energy storage device 80, such as a capacitor or a storage battery. Energy stored in the energy storage device 80 may be used to power both the oxygen sensor 46 and the heating element 76. It should be understood that current generated by the rotational power generation device 64 may be adjusted to a requisite level by adjusting the power output. Additionally, the size of the energy storage device 80 will determine the amount of electricity available for storage.

Next, the exhaust gas flows through holes 79 in a protective shield 81 covering the tip region 60. Oxygen ions in the exhaust gases react with the electrode 58. Similarly, air enters the cap region 62 through holes 82 in an outer shell 84. Oxygen ions in the air also react with the electrode 58. This series of reactions creates an electrical charge in the zirconia ceramic. The strength of the charge depends upon the number of oxygen ions passing through the zirconia ceramic. The inner and outer platinum surfaces 72, 74 accumulate the charge and carry it to an on-board signal communication device 90 for further analysis by the PCM 20.

FIG. 4 depicts the power generation device 64 and the generator 78, both of which may be attached to, or integrally formed as part of the tip region 60 of the first oxygen sensor 46. Referring now to FIG. 5, the cap region 62 is depicted in greater detail. The cap region 62 of the oxygen sensor 46 may include the energy storage device 80, the on-board signal communication device 90, and an integrated circuit (IC) chip 92. The IC chip 92 may regulate the power supplied by the energy storage device 80 to the oxygen sensor 46 and the heating element 76. Additionally, the IC chip 92 sends signals indicating a rich or lean oxygen condition between the oxygen sensor 46 and the PCM 20 through the on-board signal communication device 90. A similar wireless communication device 94 is located in the PCM 20 to wirelessly receive the signals. It should be understood that the IC chip 92, through the signal communication device 90, is also capable of receiving signals and commands transmitted by the PCM 20 from the wireless communication device 94.

Figure 6:
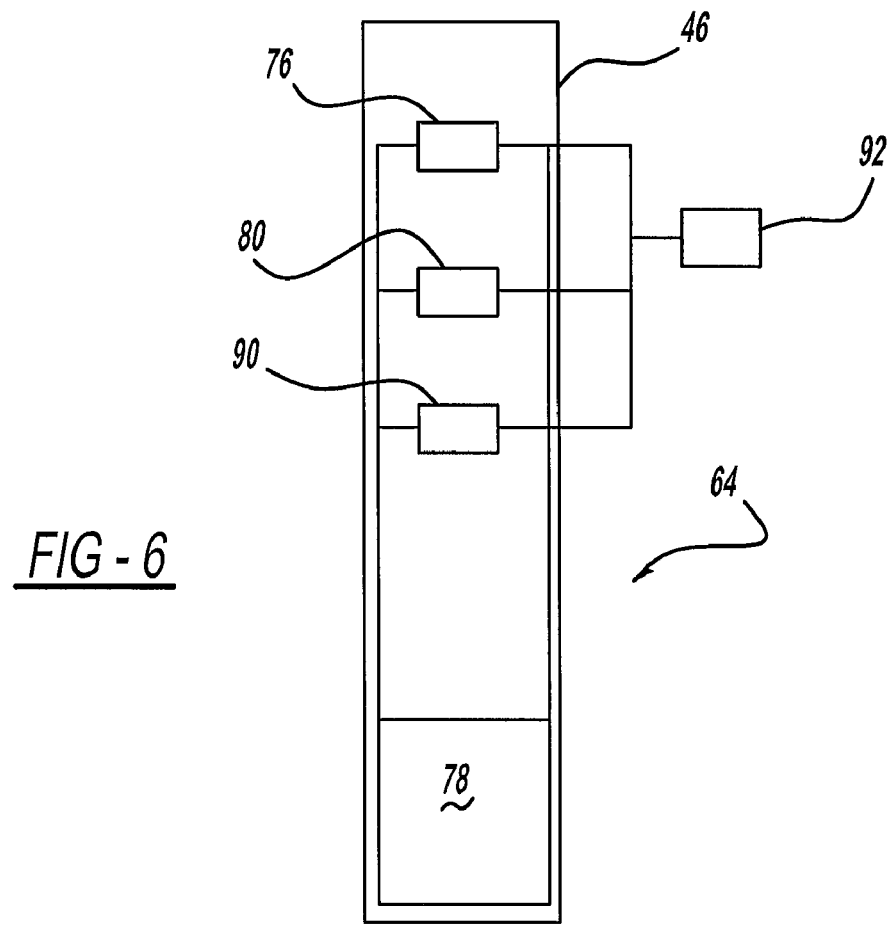
FIG. 6 is a schematic of electrical connections between the power generation device used to generate electricity and oxygen sensor components.

FIG. 6 depicts an electrical wiring diagram of how the rotational power generator 64 may supply direct electrical power to the heating element and energy storage device 80, such as a capacitor or battery. When the rotational power generator 64 generates electricity, such as by turning a generator using the flow of the exhaust gas 47 to rotate blades 49, for example, the electricity may then be supplied to the heating element 76, signal communication device 90, energy storage device 80 and the IC chip 92. In essence, the rotational power generator 64 supplied electricity to electrically power the entire first oxygen sensor 46. As a result, because the first oxygen sensor 46 is entirely electrically powered by the rotational electrical generator 78, no external wires are necessary for connection to the sensor 46 to electrically power it using an outside source of energy, such as a vehicle alternator or the engine's main starting battery.

What has been disclosed then is an apparatus utilizing an oxygen sensor 46 in an exhaust system 16 of a motor vehicle 11. The apparatus may employ an oxygen sensor 46 with an outer shell 84, an electrode 58 disposed in the outer shell 84, the electrode 58 for measuring an amount or quantity of oxygen in an exhaust gas 47 passing through a tail pipe 96 of the motor vehicle 11 and for generating a signal based on the measured amount of oxygen. Continuing, the apparatus may employ a first wireless communication device 90 disposed within the outer shell 84 for wirelessly transmitting the signal from the electrode 58, an integrated circuit chip 92 for controlling functions of the oxygen sensor 46, and an energy or power-storing device 80 within the outer shell 84 to provide power to at least the first wireless communication device 90 and the integrated circuit chip 92. The apparatus may also employ an electrical power generation device 64 disposed in the tail pipe 96, the power generation device 64 for supplying electrical power to the power-storing device 80. An electrical generator 78 may be part of the rotational power generation device 64. The electrical generator 78 may be rotatably driven by the exhaust gas 47 using a turbine or fan with blades 49. The rotation of the fan blades 49 turn the generator 78 to generate electrical current in the generator 78 for storage in the power-storing device 80, such as a battery or capacitor. The power generation device 64 may be connected to the oxygen sensor 46 or may be physically separate (e.g. with space between the two) from the oxygen sensor 46. More specifically, the power generation device 64 may be connected by welding, bolting, integral molding, etc. to the oxygen sensor 46 or the power generation device 64 may not be physically connected to the oxygen sensor 46. The power generation device 64 may be physically separate from the oxygen sensor 46 and its outer shell 84. The power generation device 64 may be connected to any section or length of the exhaust system 16, including the tail pipe 96.

A heating element 76 within the oxygen sensor 46 may be supplied with electrical power directly from the power generation device 64. Additionally, the apparatus may employ a vehicle powertrain control module 20 and a second wireless communication device 94 in the powertrain control module 20 for wirelessly receiving the signal from the communication device 90. The second wireless communication device 94 may transmit a command that is receivable by the first wireless communication device 90. The measured amount of oxygen as measured by the oxygen sensor 46 reacts with the electrode 58 to generate the signal(s), which may be one of a voltage and a resistance.

In another example of the teachings of the present disclosure, an apparatus may utilize an oxygen sensor 46 in an exhaust system 16 of a motor vehicle 11. The apparatus may further employ an outer shell 84 of the oxygen sensor 46 with an electrode 58 disposed in that outer shell 84. The electrode 58 for measuring an amount of oxygen in an exhaust gas 47 passing through a tail pipe 96 of the exhaust system 16 of the motor vehicle 11 and for generating a signal based on the measured amount of oxygen. A first wireless communication device 90 may be disposed within the outer shell 84 of the oxygen sensor 46 for wirelessly transmitting the signal from the electrode 58. An integrated circuit chip 92 may control functions of the oxygen sensor 46, such as the sensor's calibration and sensitivity. An energy or power-storing device 80 may also reside within the outer shell 84 to provide power to at least the first wireless communication device 90 and the integrated circuit chip 92. A power generation device 64 may be positioned through a wall of any section of the exhaust system 16, such as the tail pipe 96 or downpipe 44, as examples, and be exposed to an interior volume of the tail pipe 96, such as where exhaust gases 47 flow with a velocity. The power generation device 64 may generate and supply electrical power to the power-storing device 80.

In yet another example of the teachings of the present disclosure, an apparatus may utilize an oxygen sensor 46 in an exhaust system 16 of a motor vehicle 11. The apparatus may further employ an electrode 58 disposed within an outer shell 84 of the electrode 58, which measures an amount of oxygen in an exhaust gas 47 passing through a tail pipe 96, or any length of an overall exhaust system 16 of a motor vehicle 11. The electrode 58 may generate a signal, represented as a voltage or current, based on the measured amount of oxygen in the exhaust gas 47, and the signal may be transmitted by a first wireless communication device 90 disposed within the outer shell 84. The first wireless communication device 90 may wirelessly transmit the signal from the electrode 58 while an integrated circuit chip 92 may control functions of the oxygen sensor 46, such as calibration or working order of the oxygen sensor. A power-storing device 80, such as a capacitor or storage battery, may be located within the outer shell 84 to provide power to at least the first wireless communication device 90 and the integrated circuit chip 92. A power generation device 64 may employ a plurality of blades 49, such as fan or turbine blades, that rotate on an axis to turn an electrical generator 78 to generate electrical energy and supply electrical power to the power-storing device 80. The power generator device 64 may be positioned through a wall of the exhaust system 16, such as the tail pipe 96, and be exposed to an interior volume of the tail pipe 96.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An apparatus utilizing an oxygen sensor in an exhaust system of a motor vehicle, the apparatus comprising:
    an outer shell;
    an electrode disposed in the outer shell, the electrode measuring an amount of oxygen in an exhaust gas passing through a tail pipe of the motor vehicle and generating a signal based on the measured amount of oxygen;
    a first wireless communication device disposed within the outer shell wirelessly transmitting the signal from the electrode;
    an integrated circuit chip controlling functions of the oxygen sensor; and
    a power-storing device within the outer shell providing power to at least the first wireless communication device and the integrated circuit chip.

2. The apparatus of claim 1, further comprising:
a rotational power generation device disposed in the tail pipe, the power generation device for supplying electrical power to the power-storing device.

3. The apparatus of claim 2, further comprising:
an electrical generator as part of the rotational power generation device, wherein the electrical generator is rotatably driven by the exhaust gas and the rotation generates an electrical current for storage in the power-storing device.

4. The apparatus of claim 3, wherein the rotational power generation device is connected to the oxygen sensor.

5. The apparatus of claim 3, wherein the rotational power generation device is not connected to the oxygen sensor and is connected to the tail pipe.

6. The apparatus of claim 3, further comprising:
a heating element, wherein the rotational power generation device supplies electrical power directly to the heating element.

7. The apparatus of claim 1, further comprising:
a vehicle powertrain control module; and
a second wireless communication device in the powertrain control module wirelessly receiving the signal from the communication device.

8. The apparatus of claim 7, wherein the second wireless communication device may transmit a command that is receivable by the first wireless communication device.

9. The apparatus of claim 8, wherein the measured amount of oxygen reacts with the electrode to generate the signal and the signal is one of a voltage and a resistance.

10. An apparatus utilizing an oxygen sensor in an exhaust system of a motor vehicle, the apparatus comprising:
an outer shell;
an electrode disposed in the outer shell, the electrode measuring an amount of oxygen in an exhaust gas passing through a tail pipe of the motor vehicle and generating a signal based on the measured amount of oxygen;
a first wireless communication device disposed within the outer shell wirelessly transmitting the signal from the electrode;
an integrated circuit chip controlling functions of the oxygen sensor;
a power-storing device within the outer shell providing power to at least the first wireless communication device and the integrated circuit chip; and
a rotational power generation device positioned through a wall of the tail pipe and exposed to an interior volume of the tail pipe, the rotational power generation device for generating and supplying electrical power to the power-storing device.

11. The apparatus of claim 10, wherein the rotational power generation device is connected to the oxygen sensor.

12. The apparatus of claim 10, wherein the rotational power generation device is physically separate from the oxygen sensor and connected to the tail pipe wall.

13. The apparatus of claim 10, further comprising:
a heating element, wherein the rotational power generation device supplies electrical power directly to the heating element.

14. The apparatus of claim 13, further comprising:
a vehicle powertrain control module; and
a second wireless communication device in the powertrain control module for wirelessly receiving the signal from the communication device.

15. The apparatus of claim 14, wherein the second wireless communication device may transmit a command that is receivable by the first wireless communication device in the oxygen sensor.

16. The apparatus of claim 15, wherein the measured amount of oxygen reacts with the electrode to generate the signal and the signal is one of a voltage and a resistance.

17. The apparatus of claim 16, wherein the power-storing device is a capacitor.

18. The apparatus of claim 17, wherein the power-storing device is a battery.

19. An apparatus utilizing an oxygen sensor in an exhaust system of a motor vehicle, the apparatus comprising:
an outer shell;
an electrode disposed in the outer shell, the electrode measuring an amount of oxygen in an exhaust gas passing through a tail pipe of the motor vehicle and generating a signal based on the measured amount of oxygen;
a first wireless communication device disposed within the outer shell wirelessly transmitting the signal from the electrode;
an integrated circuit chip controlling functions of the oxygen sensor; and
a power generation device comprising:
a plurality of blades that rotate to turn an electrical generator, the power generator device positioned through a wall of the tail pipe and exposed to an interior volume of the tail pipe, the power generation device generating and supplying electrical power to the power-storing device.

20. The apparatus of claim 19, further comprising:
a power-storing device within the outer shell providing power to at least the first wireless communication device and the integrated circuit chip, wherein the power generation device is connected to the oxygen sensor.

\* \* \* \* \*